(12) United States Patent
Lim et al.

(10) Patent No.: US 7,858,361 B2
(45) Date of Patent: Dec. 28, 2010

(54) TRANSFORMED SACCHAROMYCES CEREVISIAE AND METHOD FOR MASS-PRODUCTION OF LK8 PROTEIN USING THE SAME

(75) Inventors: Hyung-Kwon Lim, Gyunggi-do (KR); Jung Hwan Park, Seoul (KR); Sung-Geun Kim, Gyunggi-do (KR)

(73) Assignee: Mogam Biotechnology Research Institute, Guynggi-Do (KR)

( * ) Notice: Subject to any disclaimer, the term of this patent is extended or adjusted under 35 U.S.C. 154(b) by 1044 days.

(21) Appl. No.: 10/587,155

(22) PCT Filed: Jan. 26, 2005

(86) PCT No.: PCT/KR2005/000214
§ 371 (c)(1),
(2), (4) Date: Jul. 25, 2006

(87) PCT Pub. No.: WO2005/071074
PCT Pub. Date: Aug. 4, 2005

(65) Prior Publication Data
US 2008/0187940 A1 Aug. 7, 2008

(30) Foreign Application Priority Data
Jan. 27, 2004 (KR) ...................... 10-2004-0005033

(51) Int. Cl.
*C12N 1/00* (2006.01)
(52) U.S. Cl. .................................................. 435/255.1
(58) Field of Classification Search ........................ None
See application file for complete search history.

(56) References Cited

U.S. PATENT DOCUMENTS

| 7,270,969 B2 * | 9/2007 | Watt et al. ................... 435/7.37 |
| 2007/0031379 A1 * | 2/2007 | Lee et al. .................... 424/93.2 |

FOREIGN PATENT DOCUMENTS

| WO | WO0119868 | * | 3/2001 |
| WO | WO 03/10020 | * | 12/2003 |

OTHER PUBLICATIONS

Lee et al. Improved efficiency and stability of multiple cloned gene insertions at the sigma sequences of *Saccharomyces cerevisiae*. Appl. Microbiol. Biotechnol. 48: 339-345, 1997.*
Kumar et al. Investigations into the polymorphisms at the ECM38 locus of two widely used *Saccharomyces cerevisiae* S288C strains, YPH499 and BY4742. Yeast. Jul. 30, 2003;20(10):857-63.*
Brake et al. Alpha-factor-directed synthesis and secretion of mature foreign proteins in *Saccharomyces cerevisiae*. Proc Natl Acad Sci U S A. Aug. 1984;81(15):4642-6.*
Osborne et al. Mutational analysis of a yeast transcriptional terminator. Proc Natl Acad Sci U S A. Jun. 1989;86(11):4097-101.*
Sanchez-Torres et al. A cellulase gene from a new alkalophilic *Bacillus sp.* (strain N186-1). Its cloning, nucleotide sequence and expression in *Escherichia coli*. Appl Microbiol Biotechnol. Sep. 1996;46(2):149-55.*
pET12a plasmid map. http://www.merck-chemicals.com/life-science-research/vector-table-novagen-pet-vector-table/c_HdSb.s1O77QAAAEhPqsLdcab. 1998.*
Cha et al. Selection of optimum expression system for production of kringle fragment of human apolipoprotein(a) in *Saccharomyces cerevisiae*. Biotechnology and Bioprocess Engineering. vol. 9, No. 6 / Dec. 2004, pp. 523-527.*
Folkman et al, "Angiogenesis", The Journal of Biological Chemistry 267(16):10931-10934, 1992.
Vicki Brower, "Tumor angiogenesis-new drugs on the block", Nature Biotechnology 17:396-968, 1999.
Carmeliet et al., "Angiogenesis in cancer and other diseases", Nature 407:249-257, 2000.
Kim, M. et al., "Enhanced production of anticoagulant hirudin in recombinant *Saccharomyces cerevisiae* by chromosomal s-integration," Journal of Biotechnology, 85 (2001) 41-48.
Cho, K. et al., "s-Integration of endo/exo-glucanase and B-glucosidase genes into the yeast chromosomes for direct conversion of cellulose to ethanol," Enzyme and Microbial Technology, 25 (1999) 23-30.
Lee, D. et al., "Expression of hirudin in fed-batch cultures of recombinant *Saccharomyces cerevisiae*," Biotechnology Letters, vol. 16, No. 7 (Jul. 1999) pp. 667-670.
Ferreira, B. et al., "Towards a cost effective strategy for cutinase production by a recominant *Saccharomyces cerevisiae*: strain physiological aspects," Appl. Microbial Biotechnol (2003) 61: 69-76.
Calado, C. et al., "Development of a fed-batch cultivation strategy for the enhanced production and secretion of cutinase by a recombinant *Saccharomyces cerevisiae* SU50 strain," Journal of Bioscience and Bioengineering, vol. 96, No. 2 (2003) 141-148.
Kim, J. et al., "Human apolipoprotein(a) kringle V inhibits angiogenesis in vitro and in vivo by interfering with the activation of focal adhesion kinases," Biochemical and Biophysical Research Communications 313 (2004) 534-540.
Wang, X. et al., "G418 selection and stability of cloned genes integrated at chromosomal s sequences of *Saccharomyces cerevisiae*," Biotechnology and Bioengineering, vol. 49 (1996) 45-51.

* cited by examiner

*Primary Examiner*—Michele K Joike
(74) *Attorney, Agent, or Firm*—Gates & Cooper LLP

(57) ABSTRACT

The present invention relates to a method for preparing LK8 protein, more precisely, a method for mass-production of LK8 protein using *Saccharomyces cerevisiae* transformed by a gene coding LK8 protein having angiogenesis inhibiting activity. The transformed strain of the present invention and production processes of LK8 protein are expected to contribute greatly to the commercialization of LK8 protein as a novel angiogenesis inhibitor.

1 Claim, 14 Drawing Sheets

SEQUENCE LISTING

```
<160> NUMBER OF SEQ ID NOS: 2

<210> SEQ ID NO 1
<211> LENGTH: 258
<212> TYPE: DNA
<213> ORGANISM: Homo sapiens
<220> FEATURE:
<221> NAME/KEY: gene
<222> LOCATION: (1)...(258)
<223> OTHER INFORMATION: LK8 cDNA

<400> SEQUENCE: 1
gaacaggact gcatgtttgg gaatgggaaa ggataccggg gcaagaaggc aaccactgtt      60
actgggacgc catgccagga atgggctgcc caggagcccc atagacacag cacgttcatt     120
ccagggacaa ataaatgggc aggtctggaa aaaaattact gccgtaaccc tgatggtgac     180
atcaatggtc cctggtgcta cacaatgaat ccaagaaaac tttttgacta ctgtgatatc     240
cctctctgtg catcctct                                                   258

<210> SEQ ID NO 2
<211> LENGTH: 255
<212> TYPE: DNA
<213> ORGANISM: Saccharomyces cerevisiae
<220> FEATURE:
<221> NAME/KEY: sig_peptide
<222> LOCATION: (1)...(255)
<223> OTHER INFORMATION: alpha-factor secretion signal

<400> SEQUENCE: 2
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc catttccaa cagcacaaat      180 aacgggttat tgtttataaa tactactatt gccagcattg ctgctaaaga agaagggta      240 tctctcgaga aaaga                                                      255
```

TRANSFORMED SACCHAROMYCES CEREVISIAE AND METHOD FOR MASS-PRODUCTION OF LK8 PROTEIN USING THE SAME

TECHNICAL FIELD

The present invention relates to a method for preparing LK8 protein, more particularly, a method for mass-production of LK8 protein using *Saccharomyces cerevisiae* transformed by a gene coding LK8 protein having angiogenesis inhibiting activity.

BACKGROUND ART

Angiogenesis is a biological process to provide a new blood vessel to organs or tissues. Particularly, new blood capillaries are generated from an old microvessel, which are growing to become blood vessels. Angiogenesis, as a normal physiological process, is observed only in limited cases in a human body, for example during the development of fetus and embryo, during the maturation of uterus, during the proliferation of placenta, during the formation of corpus luteum, and for the healing of a wound. And even for such cases, angiogenesis is accurately regulated and stopped when it finishes its job. Angiogenesis is regulated strictly by an angiogenesis regulating factor (Folkman, J., *Nature Med.*, 1: 27-31, 1995) and the phenotype of angiogenesis seems to differ from the balance between up-regulation of an angiogenesis stimulating factor and down-regulation of an angiogenesis-inhibiting factor.

Although the angiogenesis process is very complicated and sophisticated, it can be outlined as follows. First, a stimulus for angiogenesis is transmitted to an old blood vessel, resulting in the expansion of the blood vessel and the increase of membrane permeability. Second, fibrin is coming out of the expanded blood vessel and then accumulated in cytosol around the blood vessel. Third, an enzyme to decompose the basal membrane of the old blood vessel is activated. Fourth, the basal membrane is destroyed so that endothelial cells come out of the blood vessel and proliferate in cytosol around and then move again. Lastly, those endothelial cells are lined up to form a vessel, resulting in a new blood vessel.

The diseases related to angiogenesis are exemplified by inflammatory diseases including arthritis, ophthalmic diseases including diabetic retinopathy, dermatological diseases including psoriasis and cancer which is the most representative angiogenesis related disease among all other diseases (Folkman, J., *Nature Med.*, 1:27-31, 1995). In particular, angiogenesis is essential for the growth of a primary tumor and a metastatic tumor (Folkman, J., *New Engl. J. Med.*, 285:1182-1186, 1971; Folkman, J., *J. Biol. Chem.*, 267: 10931-10934, 1992). That means a tumor cannot be growing when angiogenesis is inhibited or stopped, indicating that inhibition of angiogenesis might be an effective way for long term treatment of tumors.

Therefore, it is urgently required to develop a novel angiogenesis inhibitor to inhibit or to stop angiogenesis and further to provide the inhibitor to a user by moderate prices resulted from effective mass-production of the angiogenesis inhibitor.

Angiogenesis inhibitor is regarded as one of the most favorable treatment methods for cancer because it targets blood vessels supplying nutrients to a tumor, instead of attacking directly cancer cells, which means it reduces resistance against medicine. Various inhibitors to inhibit angiogenesis in a tumor, such as natural inhibitors found in vivo, synthetic inhibitors, integrin inhibitors, signal transduction inhibitors and proteolysis inhibitors, have been verified to be effective and are on clinical test (Brower, V., *Nat. Biotechnol.*, 17:963-8, 1999; Carmeliet, P. and Jain, R. K., *Nature*, 407: 249-57, 2000). Among those inhibitors on the clinical test, LK6, LK7 and LK8, which are the $36^{th}$, $37^{th}$ and $38^{th}$ kringle subunits of Apo(a) of human apolipoprotein, stated in international patent publication WO 01/19868, have been known to have angiogenesis inhibiting activity along with activities of growth inhibition and migration inhibition of epithelial cells. Especially, LK8 protein shows the highest activity. In order to provide moderate prices for the production of LK8 protein for the examination of the effect of the protein, for clinical test and for commercial use, the development of a method for mass-production of LK8 protein through the culture of recombinant strain transformed by LK8 gene is essential.

Thus, the present inventors have studied on the functions of LK8 protein and the method for effective commercial use of the protein. At last, the present inventors prepared recombinant *Saccharomyces cerevisiae* by transforming yeast *Saccharomyces cerevisiae* with plasmid vector containing LK8 gene or inserting LK8 gene into host chromosome, and then selected strains mass-producing LK8 protein therefrom. The present inventors also determined the optimal culture condition for the growth of the strains and finally completed this invention by confirming that high quality LK8 protein could be mass-produced under said condition.

DISCLOSURE OF INVENTION

Technical Problem

It is an object of the present invention to provide a preparation method for transformed yeast strain that is able to mass-produce LK8 protein, an angiogenesis inhibitor, and a method for mass-production of LK8 protein by the culture of the strain.

Technical Solution

In order to achieve the above object, the present invention provides a MδLK8 recombinant expression vector containing LK8 expression cassette consisting of promoter, secretion sequence, LK8 cDNA represented by SEQ ID No: 1 and terminator, in that order.

The present invention also provides a transformed *Saccharomyces cerevisiae* strain prepared by transfecting host strain with said recombinant vector.

The present invention further provides a method for preparing a transformant expressing LK8 protein highly, comprising the following steps: (1) transforming host strain with the recombinant vector mentioned above; (2) culturing the transformant prepared in the step 1 after the treatment of G418 sulfate antibiotics; and (3) screening LK8 high expressing transformant by immunoassay.

The present invention also provides a method for mass-production of LK8 protein, comprising the following steps: (1) preparing a transformed strain by inserting recombinant LK8 gene expression vector, MdLK8, into host strain (2) seed-culturing the transformed strain prepared in the step 1 and batch-culturing the strain in a liquid medium containing glucose and galactose as a carbon source, with keeping dissolved oxygen stable by regulating air supply and stirring speed; (3) fed-batch-culturing the culture solution of the step 2 in a liquid medium containing galactose as a carbon source; and (4) purifying LK8 protein from the culture solution of the step 3.

Hereinafter, the present invention is described in detail.

The present invention provides a MδLK8 recombinant expression vector containing LK8 expression cassette comprising promoter, secretion sequence, LK8 cDNA represented by SEQ ID No: 1 and terminator in that order, δ sequence for the multiple insertion of LK8 expression cassette into chromosome of host strain, and neomycin resistant gene (neo) for the selection after the multiple insertion. In a preferred embodiment of MδLK8 recombinant expression vector of the present invention, said promoter is GAL1 promoter. In a preferred embodiment of the present invention, said secretion sequence is α-factor secretion signal represented by SEQ ID No: 2. In another preferred embodiment of the present invetion, said terminator is CYC1 terminator.

Particularly, herein, DNA fragment containing α-factor secretion signal and LK8 cDNA was obtained by treating a restriction enzyme to pMBRI-LK8 expression vector (Korean Patent Publication No: 2004-0069840) which used to be used for the production of LK8 protein in Pichia pastoris yeast strain (see FIG. 1). The DNA fragment was inserted into p426GAL1 vector to construct expression vector pMCLK8 (6.9 kb) available for the production of recombinant LK8 expression cassette in yeast strain (see FIG. 2). Then, recombinant MδLK8 expression vector was constructed (see FIG. 5) to insert the recombinant LK8 expression cassette containing promoter, secretion sequence, LK8 cDNA sequence and terminator, into yeast chromosome, followed by multiple insertion.

The present invention also provides a transformed Saccharomyces cerevisiae strain prepared by transfecting host strain with the above recombinant expression vector. In a preferred embodiment of the transformed Saccharomyces cerevisiae of the present invention, said host strain is selected from a group consisting of Saccharomyces cerevisiae BJ3501, Saccharomyces cerevisiae BY4742, Saccharomyces cerevisiae CEN.PK2-1D and Saccharomyces cerevisiae 2805. In a more preferred embodiment of the transformed Saccharomyces cerevisiae of the present invention, said host strain is Saccharomyces cerevisiae BJ3501.

Herein, a host strain, Saccharomyces cerevisiae BJ3501, was transformed by being transfected with recombinant expression vector containing LK8 gene and then, transformed yeast strains that specifically had numbers of LK8 gene in their chromosomes were selected. The strain over-secreting LK8 protein was selected by means of colony immunoblotting, dot-blotting and ELISA (Enzyme Linked Immunosorbent assays), and then named Saccharomyces cerevisiae BJ3501/MδLK8 #36 (see FIG. 6 and FIG. 7). The strain was deposited at Korean Collection for Type Cultures of Korean Research Institute of Bioscience and Biotechnology (#52, Aeun-dong yousung-ku, Daejeun city, Korea) on Jan. 13, 2004 (Accession No: KCTC 10582BP).

The present invention further provides a method for preparing a transformant expressing LK8 proetin highly, comprising the following steps: (1) transforming host strain with the recombinant vector mentioned above; (2) culturing the transformant prepared in the step 1 after the treatment of G418 sulfate antibiotics; and (3) selecting LK8 high expressing transformant by immunoassay. In the step 2, antibiotics is not limited to G418 sulfate, but 5-20 g/L of G418 sulfate was preferably treated to the strain in this invention. In the step 3, a method for the selection is not limited to a specific one of immunoassay, but colony immunoblotting assay, dot blotting assay or ELISA (enzyme linked immunosorbant assay) is preferred. It is also preferred to perform the above step 3 additionally, and more preferably colony immunoblotting is performed for the primary selection and then dot blotting is performed for the second selection from the primary selected strains, and lastly ELISA is performed for the final selection from the secondly selected strains.

When LK8 is expressed in a transformed yeast strain containing a multi-copy of LK8 gene, prepared by the method of the present invention, in its chromosome, the secretion of LK8 protein doubles or triples, comparing to the conventional episomal expression method in which a foreign gene is introduced in the form of episome to express and secret the foreign protein.

The present invention also provides a method for mass-production of LK8 protein comprising the following steps: (1) preparing a transformed strain by inserting recombinant LK8 gene expression vector into host strain, (2) seed-culturing the transformed strain prepared in the step 1 and batch-culturing the strain in a liquid medium containing glucose and galactose as a carbon source, with keeping dissolved oxygen stable by regulating air supply and stirring speed; (3) fed-batch-culturing the culture solution of the step 2 in a liquid medium containing galactose as a carbon source; and (4) purifying LK8 protein from the culture solution of the step 3.

The method for mass-production of LK8 protein of the present invention is more precisely explained step by step hereinafter.

In a preferred embodiment of the method of the present invention, said step 1 is for the preparation of a transformed strain resulted from the insertion of recombinant LK8 gene expression vector into a host strain. More particularly, a recombinant vector containing LK8 expression cassette is introduced into a host strain, so that the expression or the secretion of LK8 gene is induced on plasmid. Then, multiple insertion of LK8 gene and secretion sequence into chromosome of the strain is performed. The strain that shows the best LK8 expression/secretion is selected, which is transformed Saccharomyces cerevisiae strain.

In step 2 of the method of the present invention, the transformed strain of the above step 1 is seed-cultured, and then batch-cultured in a liquid medium containing glucose and galactose as a carbon source, during which dissolved oxygen is kept stable by regulating air supply and/or stirring speed. At this time, the preferable inoculum size of the seed culture solution is 5-10% (w/v). The batch-culture is preferably performed with 1-3 vvm (5-80 L/minute) of air supply and/or 200-1000 rpm of stirring speed, in a liquid medium containing 1-5% (w/v) glucose and 1-5% (w/v) galactose as a carbon source, in which dissolved oxygen is adjusted to 40-90% of maximum dissolved oxygen. At this time, the liquid medium can additionally include 1-50 g/L yeast extract, 1-10 g/L casamino acid, 0.1-5 g/L uracil and 0.1-5 g/L histidine.

In a preferred embodiment of the method of the present invention, said transformed yeast strain is distributed into hundreds or thousands of sterilized storage vials. It is stored under the same conditions, which is working cell bank system constructed to keep and control strain in order for them to be used as the same seed at each seed-culture for the production of a recombinant protein.

In step 2, said seed-culture is carried out for 24 hours to secure required amount of cells from the working well bank system. The batch-culture of the present invention is the stage of cell growth, during which the number of cell is increased and cells become adapted to an expression inducing agent, galactose. In the late stage of batch-culture, dissolved oxygen is decreased because of vigorous respiration of cells. In order to prevent the decrease of dissolved oxygen, air supply and stirring speed ought to be regulated until batch-culture is finished to keep dissolved oxygen 40% above.

Step 3 of the method of the present invention is for fed-batch-culture of the culture solution of step 2 in a liquid medium containing galactose as a carbon source. At this time, dissolved oxygen has to be maintained as 20-80% of maximum dissolved oxygen, and the liquid medium preferably includes 20-50% (w/v) galactose as a carbon source. It is also preferred to regulate the speed of galactose supply in order to maintain galactose content in the medium as 0.5-5% (w/v). The liquid medium can additionally include 1-50 g/L yeast extract, 1-30 g/L peptone, 0.1-5 g/L uracil and 0.1-5 g/L histidine.

The supply of galactose is controlled from the beginning of fed-batch-culture in order to maintain regular galactose content in medium. That is, the content of galactose in medium is maintained as under 5% (w/v) by adding galactose if necessary, for which dissolved oxygen has to be checked all through the culture, and as a result, the expression of LK8 protein is increased. From the fed-batch-culture, several hundred □ of LK8 protein per 1 L of culture supernatant can be obtained (see FIG. 8 and FIG. 9).

Step 4 of the method of the present invention is for purifying LK8 protein from the culture solution of the above step 3. LK8 protein is a hydrophilic molecule having 9-10 kD of molecular weight. It has characteristically low solubility in neutral pH. During its expression in culture solution, derivatives having smaller or bigger molecular weight than LK8 protein happen to be generated. Thus, in order to separate pure LK8 protein from culture solution, purifying processes taking advantage of physico-chemical characteristics of LK8 protein are required.

For the purification of LK8 protein in the present invention, any of conventional protein purifying processes can be used without limitation, but chromatography is preferred. It is more preferred for the chromatography to include ion exchange chromatography and hydrophobic interaction chromatography (see FIG. 10-FIG. 13). In a preferred embodiment of the method of the present invention, said ion exchange chromatography is cation exchange chromatography, and the elution of LK8 protein is preferably performed from the eluting solution containing 0-5 M of NaCl at pH 4.0-8.0. In the case of using hydrophobic interaction chromatography, the elution of LK8 protein is preferably performed from 100 mM of sodium phosphate eluting solution containing 0.1-5 M of ammonium sulfate and 0-500 mM of NaCl at pH 4-8.

Particularly, in a more preferred embodiment of the method of the present invention, LK8 protein is attached to cation exchange resin by means of cation exchange chromatography, then, impurities are removed by regulating pH or salinity. The elution of LK8 protein at proper concentration is performed. At this time, the level of pH and the salt concentration depend on the type of cation exchange resin. In a preferred embodiment of the method of the present invention, strong ion exchange resin of SP (sulpho propyl) is used. It is generally understood among those people in this field that when strong cation exchange chromatography is used, washing and the elution of LK8 protein are performed at high salt concentration and at high level of pH because of its stronger ionic bond, comparing to week cation exchange chromatography. Thus, the present invention is not limited to the embodiments using SP (sulpho propyl) cation exchange resin and the buffer condition, suggesting that the invention can include any purifying processes using conventional cation exchange resin to concentrate LK8 after eliminating impurities attached to LK8.

In a preferred embodiment of the method of the present invention, the resultant sample purified with said cation exchange chromatography is further purified with hydrophobic interaction chromatography. Precisely, hydrophilic LK8 protein of the sample is attached to hydrophobic resin under the high salt concentration, and then impurities are eliminated by lowering the salt concentration, followed by the elution of LK8 protein at proper salt concentration. Highly hydrophobic impurities are eliminated at the lower salt concentration than the proper salt concentration for the elution. In general, hydrophobic interaction chromatography is used for the purification of hydrophobic protein. At this time, the remaining impurities that cannot be eliminated by cation exchange resin have to be removed by taking advantage of the hydrophobic characteristics, by which purified LK8 protein can be mass-produced. However, the scope of the present invention are not limited to the above mentioned hydrophobic interaction resin and the buffer conditions. The present invention includes possible purification processes for eliminating impurities of LK8 by using conventional hydrophobic interaction resin.

MODE FOR THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Construction of Recombinant LK8 Expression Vector

A vector for the expression of a gene, containing LK8 cDNA composed of amino acid sequence of V38 of human [apolipoprotein (a)] kringle region, in yeast was constructed.

Particularly, in order to separate α-factor secretion signal and LK8 cDNA together, the present inventors used pMBRI-LK8 expression vector (Korean Patent Publication No. 2004-0069840) which has been used for the production of recombinant LK8 protein in *Pichia pastoris*. As an empty vector for the construction of pMBRI-LK8 expression vector, pPIC9 vector (8.0 kb) purchased from Invitrogen (Netherlands) was used. Precisely, AOX1 promoter of pPIC9 expression vector was used to induce the expression of LK8 gene by methanol, and to play a role in secretion of LK8 protein out of a cell which was expressed by the bond of a target gene LK8 cDNA to the region behind α-factor secretion signal. For that purpose, LK8 gene was amplified by PCR using pET15b/LK8 (International Patent Publication No. WO 01/19868) as a template. Then, the amplified gene was digested with restriction enzymes Xho I and EcoR I. Sub-cloning was performed to insert the gene fragment into pPIC9 vector, resulting in the construction of pMBRI-LK8 (8.25 kb).

Figure 1:
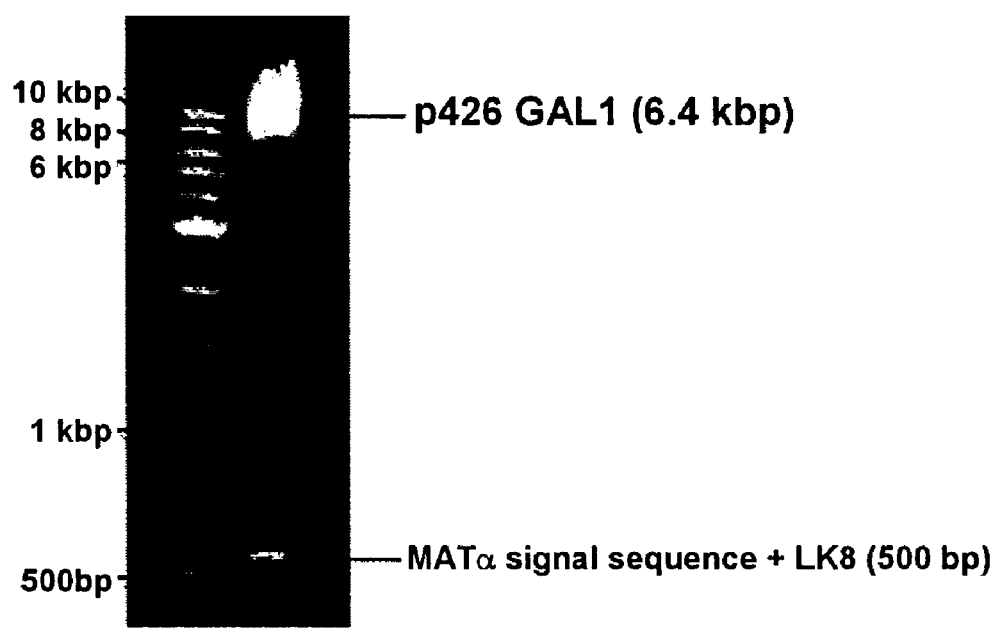
FIG. 1 is a photograph of agarose gel electrophoresis showing the GAL1 promoter DNA fragment (6.4 kbp) and DNA fragment (500 bp) containing MATα (α-factor secretion signal) represented by SEQ ID No: 2 and LK8 cDNA represented by SEQ ID No: 1 prepared by treating restriction enzymes EcoR I and BamH I to pMBRI-LK8 expression vector.
Figure 2:
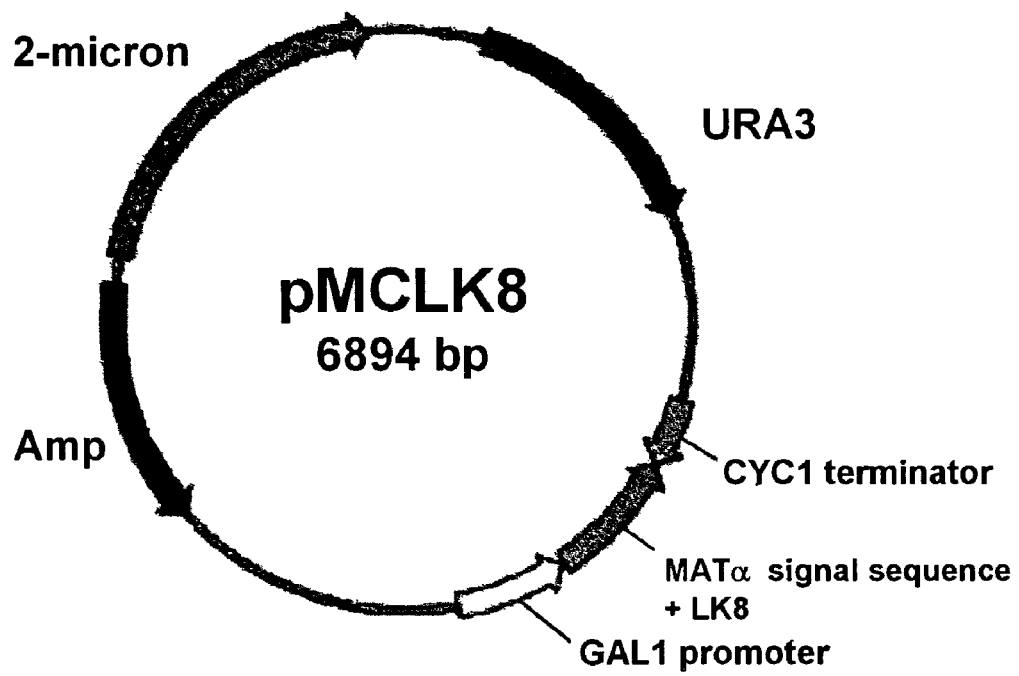
FIG. 2 is a schematic diagram showing the cleavage map of pMCLK8 (6.9 kb) expression vector constructed by inserting a DNA fragment containing α-factor secretion signal (MATα) represented by SEQ ID No: 2 and LK8 cDNA represented by SEQ ID No: 1, which are available for the production of recombinant LK8 protein in yeast, in between GAL1 promoter and CYC1 terminator of p426GAL1 vector.

The pMBRI-LK8 expression vector was treated with restriction enzyme EcoR I for 7 hours, followed by washing with PCR purification kit (Qiagen, USA). The vector was treated with restriction enzyme BamH I for 7 hours. DNA was separated by electrophoresis and DNA fragment containing α-factor secretion signal represented by SEQ ID No: 2 and nucleotide sequence of LK8 cDNA represented by SEQ ID No: 1 was obtained using gel extraction kit (QIAGEN) (FIG. 1). The obtained DNA fragment was inserted in between GAL1 promoter and CYC1 terminator of p426GAL1 vector (ATCC 87833, USA) to construct pMCLK8 expression vector (6.9 kb) for the production of recombinant LK8 in yeast (FIG. 2). Since the expression vector contains GAL1 promoter, the expression of the protein is induced by galactose. URA3 marker was used to select transformed yeast strains in a selection medium.

EXAMPLE 2

Selection of a Host Strain for the Expression of LK8 Protein

In order to select an optimum host strain for the expression of LK8 protein, BJ3501 (ATCC 208280, USA), BY4742 (EUROSCARF Y10000, Germany), CEN.PK2-1D (EUROSCARF 30000B, Germany) and 2805 (Sohn, J. H., *J. Microbiol. Biotechnol.*, 1:266-273, 1991), among many *Saccharomyces cerevisiae* strains, were selected for the experiment.

Figure 3:
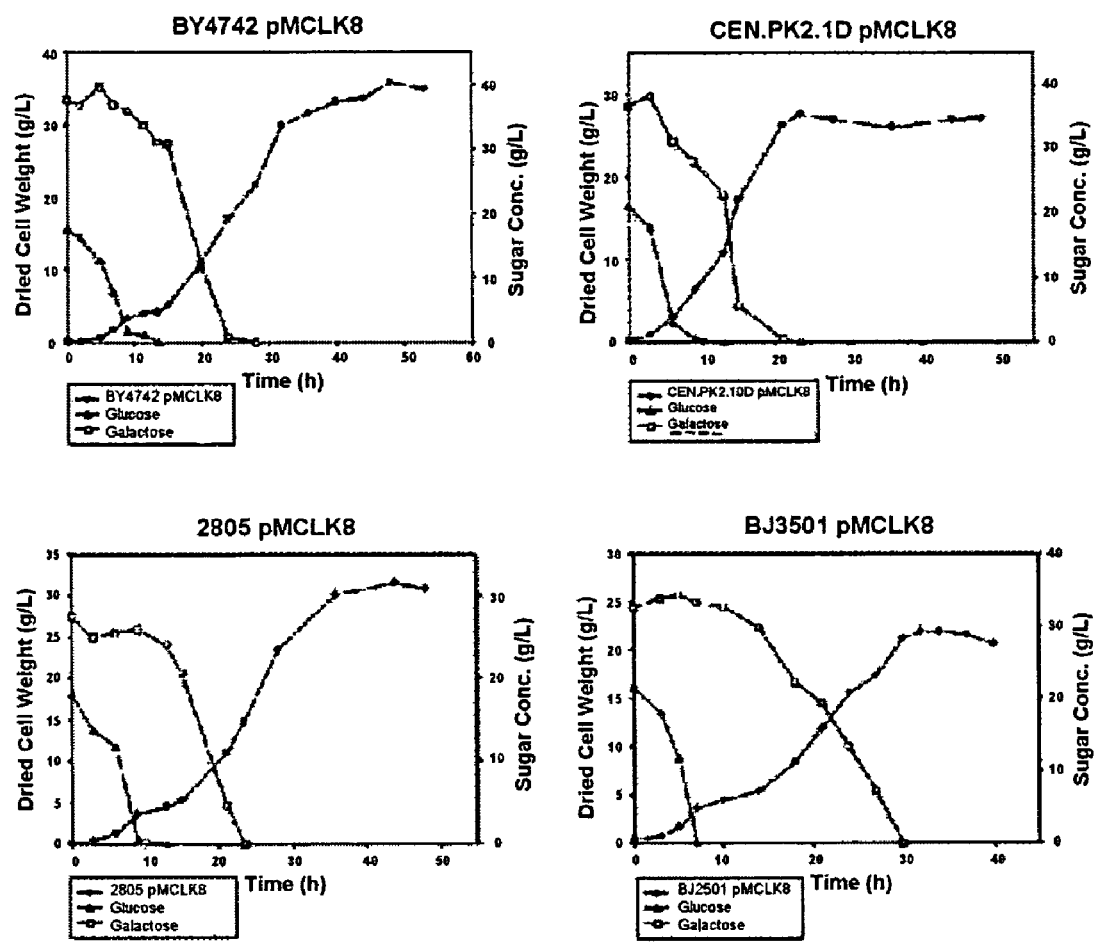
FIG. 3 is a set of graphs showing the results of liquid chromatography investigating LK8 secretion and the remaining sugar. In order to select an optimum host for the production of recombinant LK8 protein, Saccharomyces cerevisiae BJ3501, BY4742, CEN.PK2-1D and 2805 were transfected with LK8 expression vector pMCLK8 (6.9 kb). The resultant transformed yeast strains were cultured to express LK8 protein episomally.
Figure 4:
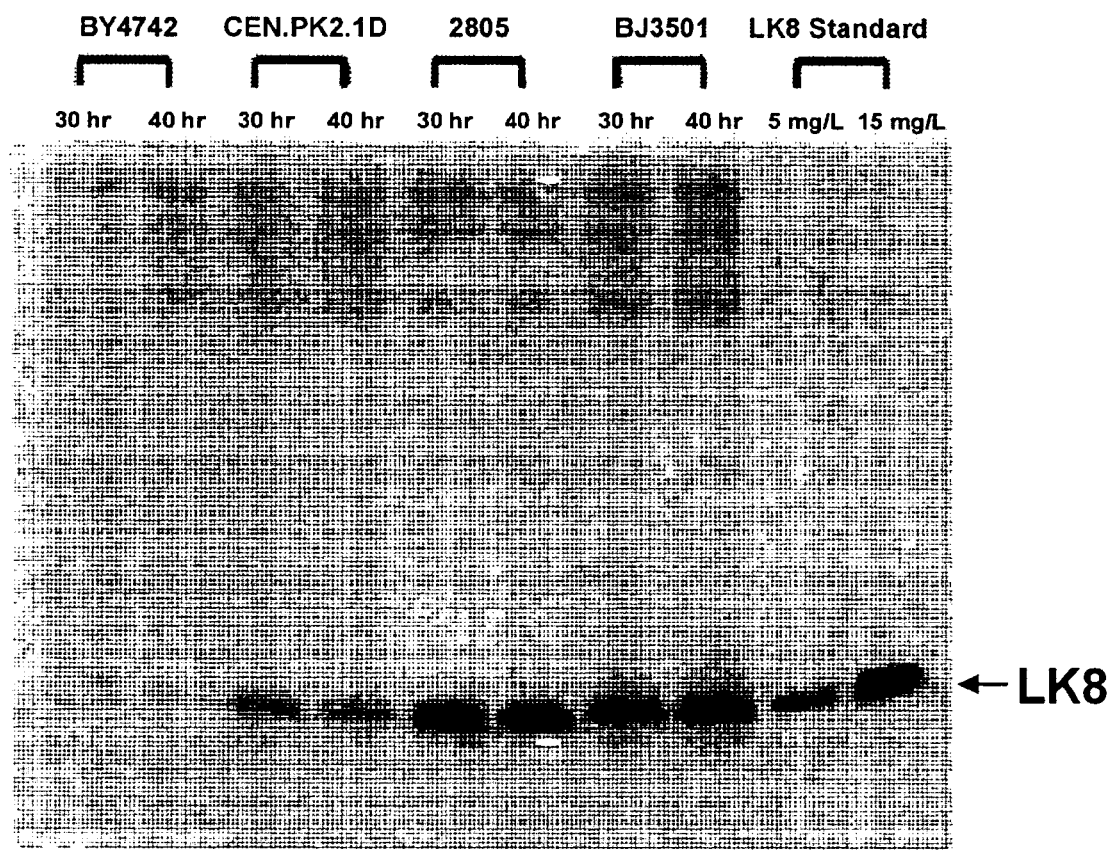
FIG. 4 is an electrophoresis photograph showing the results of immunoblotting measuring the amount of LK8 protein produced in each strain after 30 and 40 hours of culture.

Particularly, each strain mentioned above was transfected with the expression vector constructed in the above Example 1 by using alkali cation yeast kit (Q-Biogene, Canada). The strains were cultured in uracil-free yeast nitrogen base medium [(yeast nitrogen base without amino acid, Difco, USA) 0.67% and (yeast synthetic drop-out medium supplement without uracil, Difco, USA) 0.192%], in order to confirm whether or not the transformation was successfully done. For the production of recombinant LK8, each strain was cultured (30° C., pH 5.5, 700 rpm) in a bioreactor (Biostat Q, B. Braun Biotech International, Germany) with YPDG medium (2% peptone, 1% yeast extract, 2% glucose, 3% galactose). During the fermentation process, culture medium was recovered every 4 hours, and supernatant containing LK8 protein was collected by centrifugation (15,000 rpm, 5 minutes). Liquid chromatography was performed to investigate the residual sugar concentration in the culture supernatant (FIG. 3), and immunoblotting was performed to quantify the secreted recombinant LK8 protein (FIG. 4).

As a result, LK8 protein was secreted in every transformed strain, indicating that pMCLK8 expression vector was successfully introduced. In particular, *Saccharomyces cerevisiae* BJ3501 was proved to be the optimum host showing the highest secretion of LK8 protein per cell.

EXAMPLE 3

Construction of a Integration Cassette of LK8 Gene and It's Multiple-Insertion Into Yeast Chromosome A recombinant vector for the insertion of LK8 expression cassette composed of GAL1 promoter, a-factor secretion signal, nucleotide sequence of LK8 cDNA and CYC1 terminator into yeast chromosome was constructed. And a transformed yeast strain transfected with the above vector was obtained.

Figure 5:
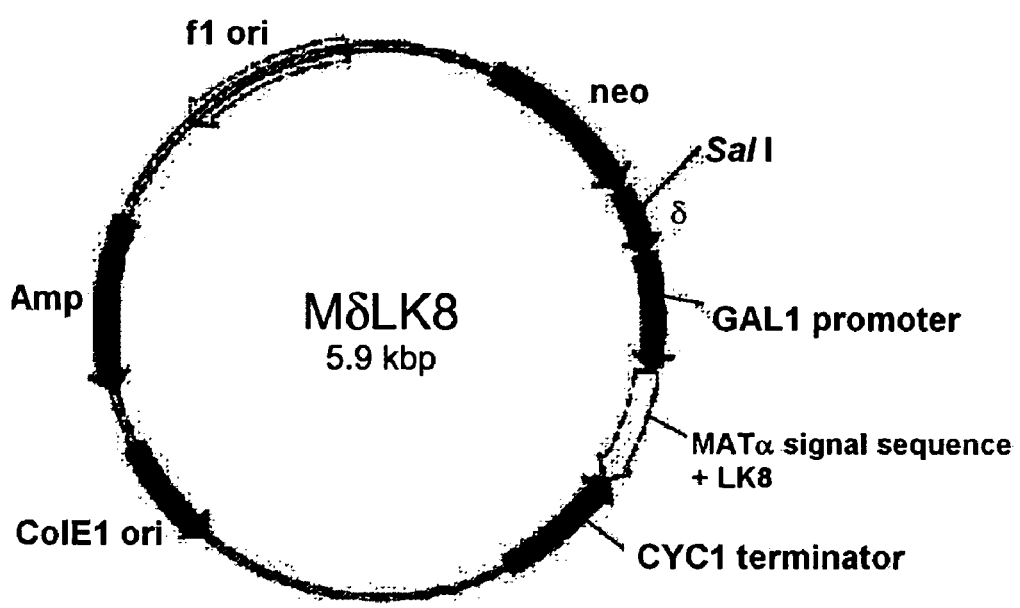
FIG. 5 is a schematic diagram showing the cleavage map of recombinant vector MδLK8 constructed to insert LK8 expression cassette containing GAL1 promoter, α-factor secretion signal represented by SEQ ID No: 2, LK8 cDNA represented by SEQ ID No: 1 and CYC1 terminator into chromosome of yeast.

Particularly, pδneo vector (Lee, FWF., *Appl. Microbiol. Biotechnol.*, 48:339, 1997) which is able to insert a target gene into δ sequence, one of transition elements of yeast chromosome, was used as a mother vector. The pδneo vector includes δ sequence enabling multiple insertion of a vector by homologous recombination and neomycin-resistant gene (neo) enabling the selection of the inserted vector. LK8 expression cassette and pδneo vector have Sal I restriction enzyme recognition site. The Sal I restriction enzyme recognition site in a recombinant vector is essential for the insertion of the vector into yeast chromosome. Thus, Sal I restriction enzyme recognition site in LK8 expression cassette was removed by using DNA blunt kit (Takara, Japan). In the meantime, LK8 expression cassette was separated from pMCLK8 vector constructed in the above Example 1 with restriction enzymes Sac I and Kpn I that cut both ends of GAL1 promoter and CYC1 terminator. Since pδneo vector did not have Kpn I restriction enzyme recognition site, both Xba I restriction enzyme recognition site of pδneo vector and Kpn I restriction enzyme recognition site of the separated LK8 expression cassette were made to be blunt end. Then, a recombinant vector was constructed by inserting LK8 expression cassette into the recombinant pδneo vector constructed above, which was named MδLK8 (FIG. 5).

The MδLK8 was linearized by treating with Sal I restriction enzyme. Then, a yeast strain was transfected with the linearized MδLK8 by using alkali cation yeast kit (Q-Biogene, Canada). In order for LK8 expression cassette to be inserted massively into yeast chromosome, the linearized MδLK8 was concentrated to 3 □/□.

Transformed yeast transfected with the linearized MδLK8 recombinant integration cassette of the present invention was selected by using YPD plate (2% peptone, 1% yeast extract, 2% glucose, 2% agar) containing G418 sulfate. At that time, the concentrations of G418 sulfate were adjusted to 5 g/L, 10 g/L and 15 g/L, respectively, to culture the transformed yeast strain.

Figure 6:
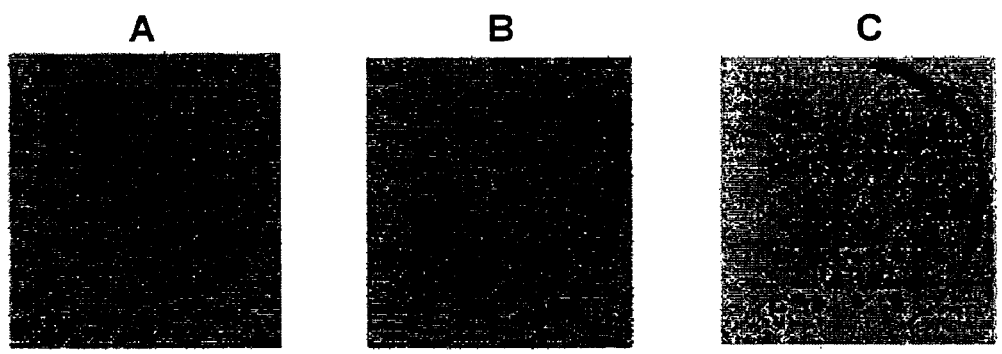
FIG. 6 is a set of photographs showing the primary screening of a strain. Precisely, colony blotting was performed to select a strain having a strong resistance against G418 sulfate, among transformed yeast strains containing LK8 expression cassette in their chromosomes. Shading on the film was observed:
A: 5 g/L of G418 sulfate treated;
B: 10 g/L of G418 sulfate treated; and
C: 15 g/L of G418 sulfate treated.

As a result, when LK8 expression cassette was massively inserted into yeast chromosome, the yeast could be growing even in a medium with high concentration of G418 sulfate and LK8 activity was also high (FIG. 6). Therefore, tens of thousands of transformed yeast colonies having resistance against G418 sulfate (even over 15 g/L concentration), owing to the mass-introduction of LK8 gene into yeast chromosome, were obtained.

EXAMPLE 4

The Primary Screening of a High-Producer of LK8 Protein by Colony Immunoblotting Among those transformed yeast strains selected in the above Example 3, the strains over-secreting LK8 protein were primarily selected by colony immunoblotting.

Particularly, transformed *Saccharomyces cerevisiae* strains were distributed on YPD solid medium, followed by culture at 30° C. for 24 hours. Then, the colony formation was observed. Sterilized cellulose membrane was put on the colony and then taken off carefully. In the meantime, nitrocellulose membrane was put on YPG solid medium, on which the above cellulose membrane was put carefully not to produce air bubble, by making the colony attached side look upward. Then, the solid medium containing colony was cultured at 30° C. for 48 hours. Cellulose membrane was carefully taken off and put on a new YPD solid medium. The remaining nitrocellulose membrane was taken off and used for blotting.

The nitrocellulose membrane was put in a solution supplemented with PBS buffer solution containing 0.1% (v/v) Tween 20® and 5% (w/v) non-fat powdered milk, which was softly stirring at room temperature for 2 hours. Rabbit LK8 antibody was put in the same solution, which was also stirred softly at room temperature for one hour, followed by washing with PBS buffer solution containing 0.1% Tween 20® five times. Anti-rabbit IgG-HRP (Sigma, USA) was put in a solution containing PBS buffer solution supplemented with 0.1% Tween 20® and 5% non-fat powdered milk, into which the nitrocellulose membrane treated above was dipped, followed by stirring softly at room temperature for one hour. It was washed five times with PBS buffer solution containing 0.1% Tween 20®. Then, the nitrocellulose membrane was taken out and transferred into a detecting solution (Pierce, USA) provided from detection kit (SuperSignal™ West Pico kit, Pierce, USA), which was fixed on radiated film. Shading on the film was investigated.

As a result, shading differed from the amount of expressed LK8 (FIG. 6), and in particular, those strains showing darker shading were primarily selected.

EXAMPLE 5

The Second Screening of a High-Producer of LK8 Protein by Dot Blotting

Among those strains selected from the primary colony screening in the above Example 4, the strains secreting LK8 protein more were secondly selected by dot blotting.

Particularly, the strains primarily selected in the Example 4 were inoculated into test tube containing YPG (2% peptone, 1% yeast extract, 2% galactose) liquid medium, followed by shaking-culture at 30° C. with 180 rpm for 48 hours. 48 hours later, the culture solution was centrifuged with 5,000 rpm for 5 minutes to obtain supernatant only. The supernatant was 10-fold diluted with PBS, which was attached onto nitrocellulose membrane by using dot blot kit (Bio-Rad, USA). The nitrocellulose membrane was left in 0.5% (v/v) glutaraldehyde solution for 5-10 minutes, and then transferred into 50 mM glycine solution, followed by washing with PBS buffer solution. Then, the nitrocellulose membrane was taken out and transferred into a detecting solution, which was fixed on radiated film. Shading on the film was investigated by detection kit in analogy to the procedure described in the above Example 4.

Figure 7:
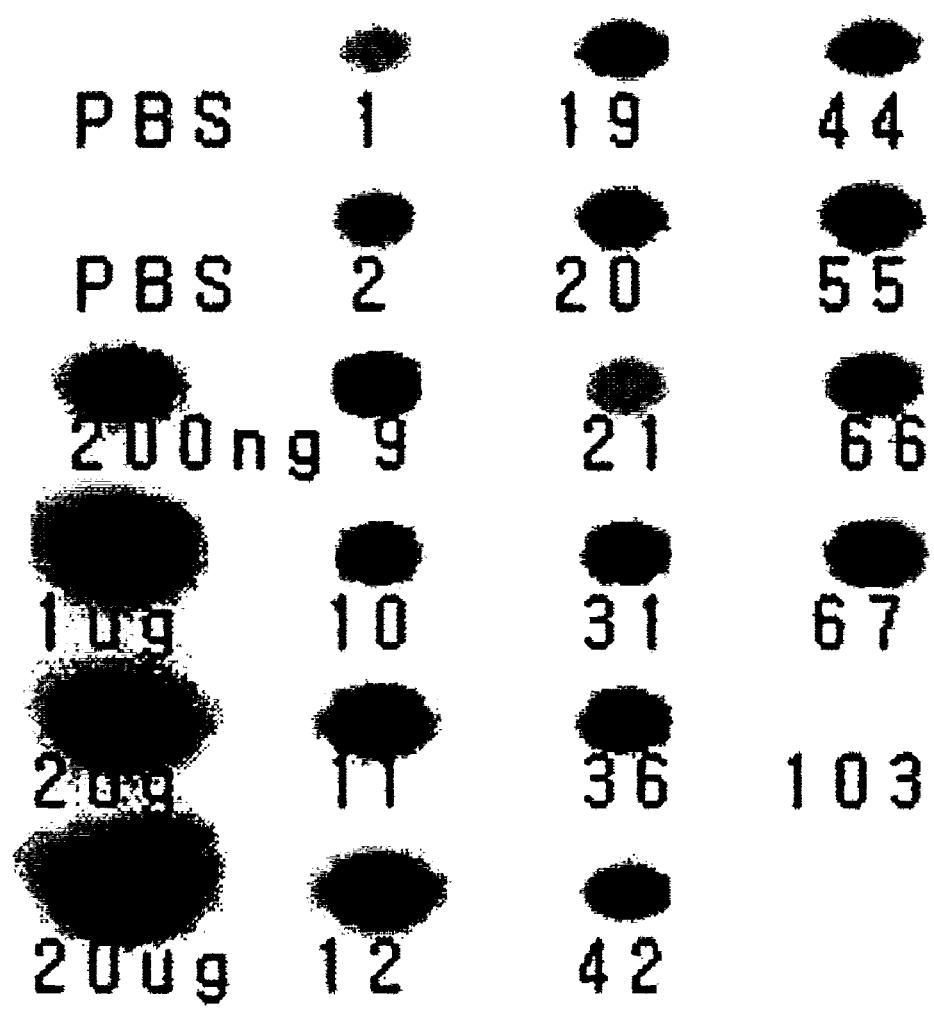
FIG. 7 is a photograph showing the second screening of a strain. The strain selected from the primary screening was fixed onto nitrocellulose membrane using dot blot kit. Then, shading on the film was observed by using a detection kit.

As a result, shading differed from the amount of expressed LK8 (FIG. 7). In particular, the strains especially showing darker shading were secondly selected.

EXAMPLE 6

The Third Screening of a High-Producer of LK8 Protein by ELISA

Among those strains selected from the second screening in the above Example 5, the strains secreting LK8 protein massively were finally selected by ELISA (Enzyme Linked Immunosorbent assay).

Particularly, the secondly selected strains were inoculated into test tube containing YPD liquid medium, followed by shaking-culture at 30° C. with 180 rpm for 48 hours. The culture solution was inoculated into a flask containing 50 ☐ of YPG liquid medium. Then, OD was adjusted by YPG liquid medium and the final volume of the flask was set to 50 ☐. Shaking-culture was performed at 30° C. with 180 rpm for 48 hours. Centrifugation with the solution was performed to obtain supernatant only.

Rabbit anti-LK8 antibodies were put on immunomodule (Maxisorp™ Immunomodule, Nunc, USA) by 0.25 ☐/well, followed by coating with a coating buffer (0.1 M sodium carbonate, pH 9.6) for ELISA. The coated immunomodule was treated with PBS buffer solution supplemented with 1% BSA (bovine serum albumin) and 0.1% Tween 20®, and then left at room temperature for 2 hours. The supernatant was 1000-fold diluted with PBS buffer solution supplemented with 0.1% Tween 20®, which was put in the immunomodule for further reaction at 37° C. for 1 hour. Then, the immunomodule was washed with PBS buffer solution supplemented with 1% BSA and 0.1% Tween 20®.

On the other hand, rat anti-LK8 antibodies were diluted with PBS buffer solution supplemented with 1% BSA and 0.1% Tween 20®. The solution was put in immunomodule, followed by reaction at 37° C. for 1 hour. When the reaction was finished, the immunomodule was washed with PBS buffer solution supplemented with 1% BSA and 0.1% Tween 20®.

For the reaction processes above, every immunomodule was colored for 15 minutes with TMB coloring reagent (TMB Peroxidase Substrates, KPL, USA), and then the coloring reaction was terminated by 1 M phosphate solution. $OD_{405}$ was measured to quantify the expression of LK8 protein.

TABLE 1

Quantification of LK8 expression by standard curve

| | Sample strain | | | | | | | | |
|---|---|---|---|---|---|---|---|---|---|
| | 1 | 102 | 11 | 17 | 25 | B9 | B12 | B31 | B36 |
| ☐/☐ | 113 | 97 | 57 | 80 | 104 | 63 | 59 | 103 | 129 |

The expression of LK8 was quantified by standard curve (Table 1). In conclusion, the strain showing the best LK8 expression was B36, which was named 'Saccharomyces cerevisiae BJ3501/MδLK8 #36'. And the strain was deposited at Korean Collection for Type Cultures of Korean Research Institute of Bioscience and Biotechnology (#52, Aeun-dong yousung-ku, Daejeun city, Korea) on Jan. 13, 2004 (Accession No: KCTC 10582BP).

Southern blot hybridization was performed to investigate the copy number of recombinant LK8 cDNA of the strain. As a result, it was confirmed that about 8 copies of LK8 gene were successfully inserted.

EXAMPLE 7

Seed-Culture Batch-Culture and Fed-Batch-Culture of Saccharomyces cerevisiae BJ3501/MδLK8 #36

<7-1> Seed-Culture

In the present invention, transformed Saccharomyces cerevisiae BJ3501/MδLK8 #36 strain was distributed into hundreds or thousands of sterilized storage vials, which were all cared under the same conditions, that is they were under the control of 'working cell bank system' established by the present inventors to keep the strain suitable as a seed for seed-culture for the production of recombinant protein. The transformed strain was cultured, as a seed, in YPD medium (1% yeast extract, 2% peptone, 2% glucose) for 24 hours to secure wanted cell mass [and activity (in the case of 20-fold dilution, $OD_{600}$=0.8-1.2)].

<7-2> Batch-Culture

Seed-culture was performed in the YPD medium. Then, batch-culture was performed in starting medium inoculated with seed-culture solution obtained in the above Example 7-1. In this stage, seed-culture solution was inoculated by over 1%, and glucose and galactose were used as a carbon source to increase the number of cells and let them be adapted to galactose. The starting medium was composed of 1-5% (w/v) glucose, 1-5% (w/v) galactose, 1-50 g/L of yeast extract, 1-10 g/L of casamino acid, 0.1-5 g/L of uracil and 0.1-5 g/L of histidine.

Air supply was regulated as 1-3 vvm and stirring speed was controlled as 200-1000 rpm according to the composition of medium. As a result, dissolved oxygen was kept over 40% during the entire batch-culture stage.

In this stage, the cell concentration reaches to over 30 of O.D. at 600 nm.

<7-3> Fed-Batch-Culture

Fed-batch-culture is the stage to increase cell mass and secretion level of LK8 protein by adding galactose that was used as an inducer and sole carbon source.

Particularly, the feed medium containing 20-50% (w/v) galactose, 1-50 g/L of yeast extract, 1-30 g/L of peptone, 0.1-5 g/L of uracil and 0.1-5 g/L of histidine was used for the fed-batch culture. At that time, in order to induce over-secretion of LK8 protein, the feed medium was supplied by the speed of 1 ☐/hr-30 ☐/hr, with keeping the content of galactose in medium as under 5% (w/v).

Figure 8:
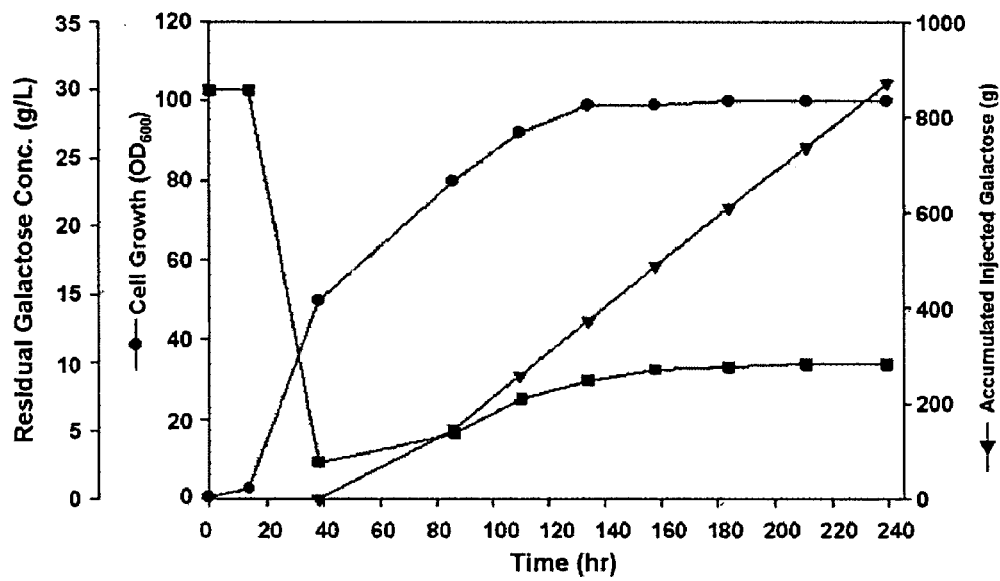
FIG. 8 is a graph showing the time-dependent cell growth (●), the accumulation of supplied galactose (▼) and the remaining galactose (■) during the fermentation processes of transformed yeast strain *Saccharomyces cerevisiae* BJ3501/MδLK8 #36.
Figure 9:
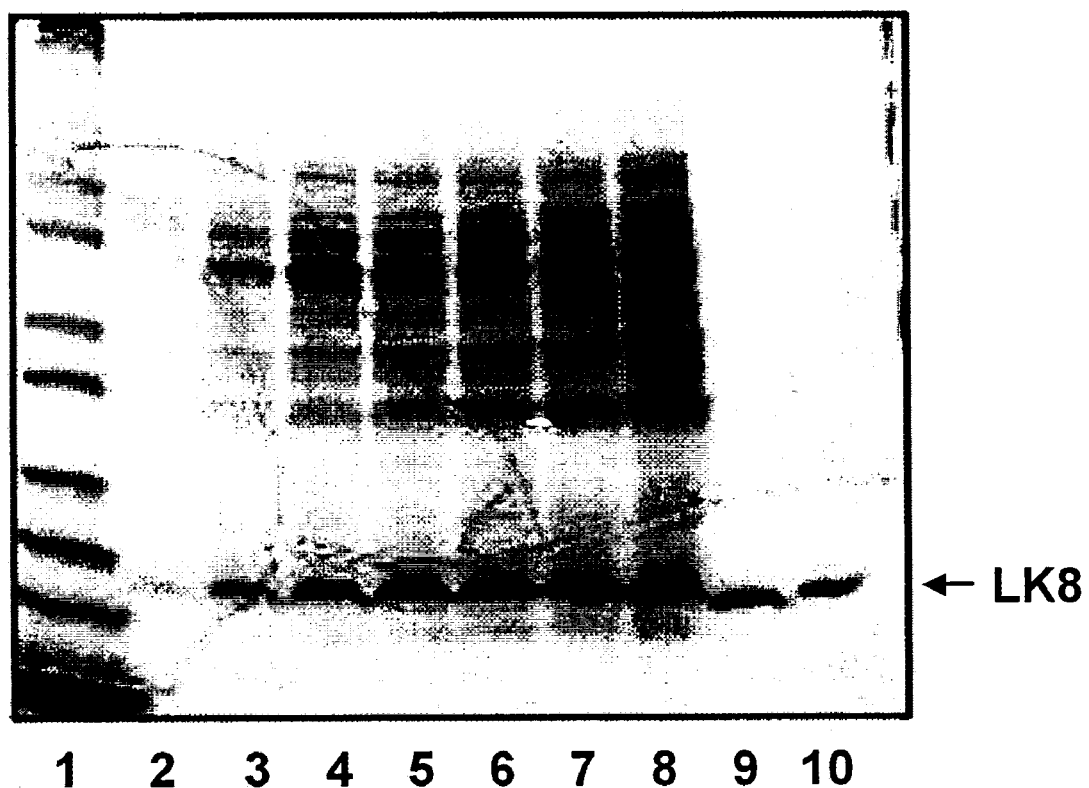
FIG. 9 is a photograph of SDS-PAGE with the culture supernatant during the fermentation of transformed yeast strain *Saccharomyces cerevisiae* BJ3501/MδLK8 #36:
Lane 1: Ladder marker;
Lane 2: 38 hours after the beginning of culture;
Lane 3: 86 hours after the beginning of culture;
Lane 4: 110 hours after the beginning of culture;
Lane 5: 134 hours after the beginning of culture;
Lane 6: 158 hours after the beginning of culture;
Lane 7: 184 hours after the beginning of culture;
Lane 8: 211 hours after the beginning of culture;
Lane 9: Control LK8 protein (200 □/L); and
Lane 10: Control LK8 protein (100 □/L).

In order to keep the concentration of galactose constantly during fed-batch culture, its content in the culture solution was measured on a regular basis and then the speed of galactose supply was controlled during whole fermentation processes, leading to the increase of LK8 expression and secretion (FIG. 8). From the fed-batch-culture, LK8 protein was secreted as much as hundreds ☐ per 1 L of culture supernatant (FIG. 9).

EXAMPLE 8

Comparison between Episomal Expression of LK8 and Chromosomal Expression of LK8

Figure 10:
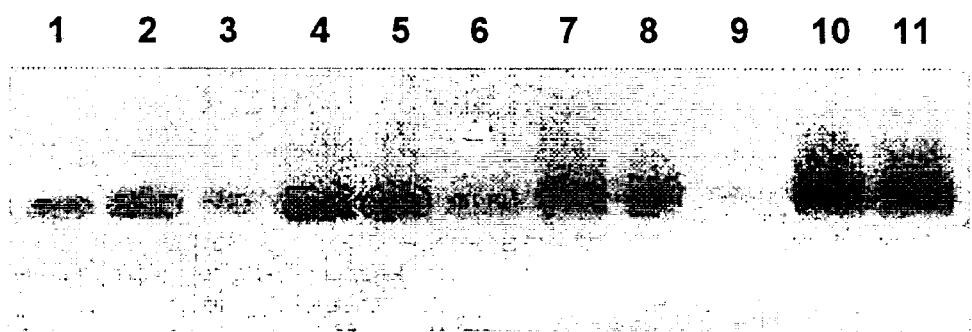
FIG. 10 is an electrophoresis photograph. In order to compare the effects of the two methods (plasmid expression of LK8 gene and expression after the insertion into chromosome) on the expression and secretion of LK8 protein, transformed yeast strains, *Saccharomyces cerevisiae* BJ3501/pMCLK8 and *Saccharomyces cerevisiae* BJ3501/MδLK8 #36, were batch-cultured. The secreted LK8 protein was quantified time-dependently by immunoblotting:
Lane 1: LK8 standard, 10 mg/L;
Lane 2: LK8 standard, 50 mg/L;
Lane 3: 20 hours after the beginning of batch-culture of *Saccharomyces cerevisiae* BJ3501/pMCLK8;
Lane 4: 30 hours after the beginning of batch-culture of *Saccharomyces cerevisiae* BJ3501/pMCLK8;
Lane 5: 40 hours after the beginning of batch-culture of *Saccharomyces cerevisiae* BJ3501/pMCLK8;
Lane 6: 20 hours after the beginning of batch-culture of *Saccharomyces cerevisiae* BJ3501/pMCLK8;
Lane 7: 30 hours after the beginning of batch-culture of *Saccharomyces cerevisiae* BJ3501/pMCLK8;
Lane 8: 40 hours after the beginning of batch-culture of *Saccharomyces cerevisiae* BJ3501/pMCLK8;
Lane 9: 20 hours after the beginning of batch-culture of *Saccharomyces cerevisiae* BJ3501/MδLK8 #36;
Lane 10: 30 hours after the beginning of batch-culture of *Saccharomyces cerevisiae* BJ3501/MδLK8 #36; and
Lane 11: 40 hours after the beginning of batch-culture of *Saccharomyces cerevisiae* BJ3501/MδLK8 #36.

In order to compare the secretion efficacy of LK8 protein between episomal expression and chromosomal expression, *Saccharomyces cerevisiae* BI3501/pMCLK8 showed the highest LK8 expression efficacy in Example 2 and *Saccharomyces cerevisiae* BI3501/MδLK8 #36 prepared in Example 6 were cultured by batch-culture method used in Example 7-2, and then the maximum LK8 secretions in them were measured (FIG. 10). As a result, as shown in FIG. 10, the LK8 secretion induced by chromosomal expression (*Saccharomyces cerevisiae* BI3501/MδLK8 #36) after 30 hours of batch-culture was twice as much as that induced by episomal expression (*Saccharomyces cerevisiae* BI3501/pMCLK8).

EXAMPLE 9

Purification of LK8 Protein by Chromatography

LK8 protein is a hydrophilic molecule having the molecular weight of 9-10 kDa, which is characterized by low solubility in neutral pH or in organic solvent. During the expression processes of LK protein, other derivatives having bigger or smaller molecular weight than LK8 protein were observed in the culture solution. Those derivatives seemed to be amino acids cut from C-terminal or N-terminal of LK8 protein or chemical derivatives. Based on such physico-chemical characteristics of LK8 protein and conditions of culture, purification process using cation exchange chromatography and hydrophobic interaction chromatography was established in this invention, in order to produce LK8 protein with high purity. Precisely, pH and salt concentration were regulated by cation exchange chromatography to eliminate impurities, followed by the elution of LK8 protein. Then, hydrophobic interaction chromatography was performed to let highly hydrophilic LK8 protein bind to fixed resin under the condition of high salt concentration. Impurities were eliminated by lowering the salt concentration. The elution of LK8 protein was carried out under the condition of proper salt concentration, then hydrophobic impurities (hydrophobic proteins, lipids or nonproteineous contaminants including endotoxins) were eliminated by lowering the salt concentration. The purification process of the present invention is more precisely explained step by step hereinafter.

<9-1> Purification by Cation Exchange Chromatography

The culture solution obtained in the Example 7 was centrifuged with 8,000 rpm to obtain supernatant. The supernatant was 4-fold diluted with 0.1-1 M sodium phosphate (monobasic) and pH was adjusted under 4. The solution was filtered by 0.45 ☐ filter membrane. A column was packed with SP-sepharose FF (fast flow) resin, followed by equilibrium with 0.1-1 M sodium phosphate solution (monobasic). Then, the diluted supernatant was loaded on the SP-sepharose column. 0.1-1 M sodium phosphate solution was passed through the column to base line. The column was washed with 0.1-1 M sodium phosphate solution (pH 5-7) to remove impurities. Then, the elution of LK8 protein was carried out by spilling 0.1-1 M sodium phosphate solution containing 0-2 M NaCl (pH 5-9).

Figure 11:
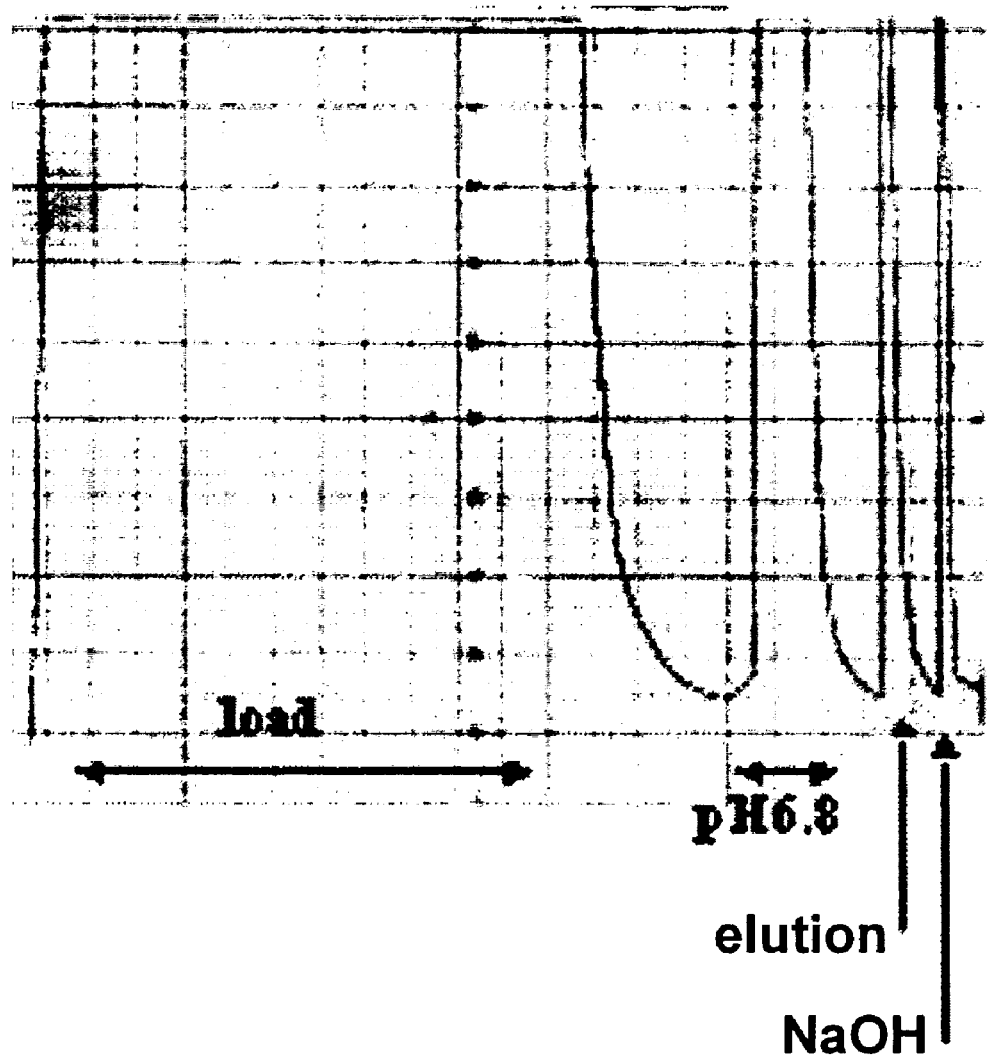
FIG. 11 is a chromatogram showing the purification step of LK8 protein by cation exchange chromatography:
Washing: 0.1-1 M of sodium phosphate solution;
Elution: 0.1-1 M of sodium phosphate, 0-2 M of NaCl solution; and
Cleaning: 0-2 M of NaCl solution.
Figure 12:
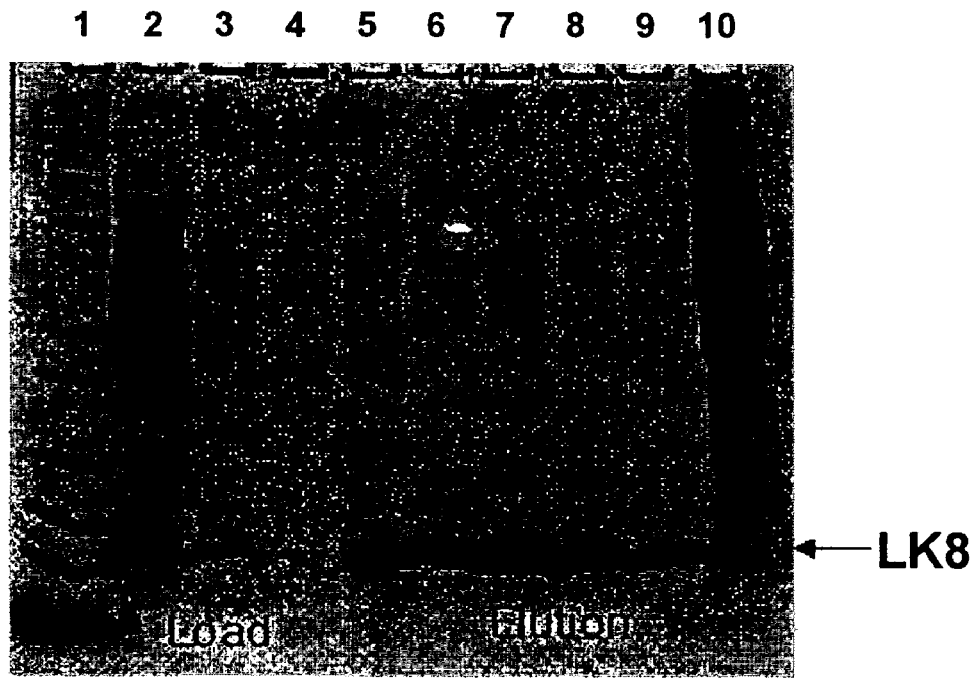
FIG. 12 is a photograph of SDS-PAGE showing the LK8 protein in each eluted fraction of SP-Sepharose cation exchange chromatography:
Lane 1: Ladder marker;
Lane 2: Supernatant of final culture solution;
Lane 3: 5-fold diluted sample of supernatant of final culture solution;
Lane 4: Diluted sample not attached resin;
Lane 5: Sample used for washing resin;
Lane 6: Eluted fraction #1;
Lane 7: Eluted fraction #2;
Lane 8: Eluted fraction #3;
Lane 9: Eluted fraction #4; and
Lane 10: Sample eluted with NaOH.

As confirmed from chromatogram (FIG. 11) and SDS-polyacryl amide gel electrophoresis (FIG. 12), most of impurities were eliminated by washing with 0.1-1 M sodium phosphate solution, and only LK8 protein was eluted from fractions by using the sodium phosphate solution containing 0-2 M NaCl.

<9-2> Purification by Hydrophobic Interaction Chromatography

A column was packed with SP-sepharose 6FF (fast flow) resin, followed by equilibrium with 0.1-1 M sodium phosphate solution (pH 5-9) containing 0.1-3 M ammonium sulfate and 0-2 M NaCl. The eluted sample of Example 9-1 was dissolved with ammonium sulfate (final conc: 0.1-3 M). Then, the solution was loaded on the SP-sepharose column. 0.1-1 M sodium phosphate solution (pH 5-9) containing 0.1-3 M ammonium sulfate and 0-2 M NaCl was passed through the column to base line. The column was washed with 0.1-1 M sodium phosphate solution (pH 5-9) containing 0.1-3 M ammonium sulfate and 0-2 M NaCl. Then, the elution of LK8 protein was carried out by spilling 0.1-1 M sodium phosphate solution (pH 5-9) containing 0.1-2 M ammonium sulfate and 0-2 M NaCl. Dialysis of the eluted LK8 protein was performed with a filter membrane (10,000 D, Sigma, USA) using 0.1-1 M sodium phosphate solution.

Figure 13:
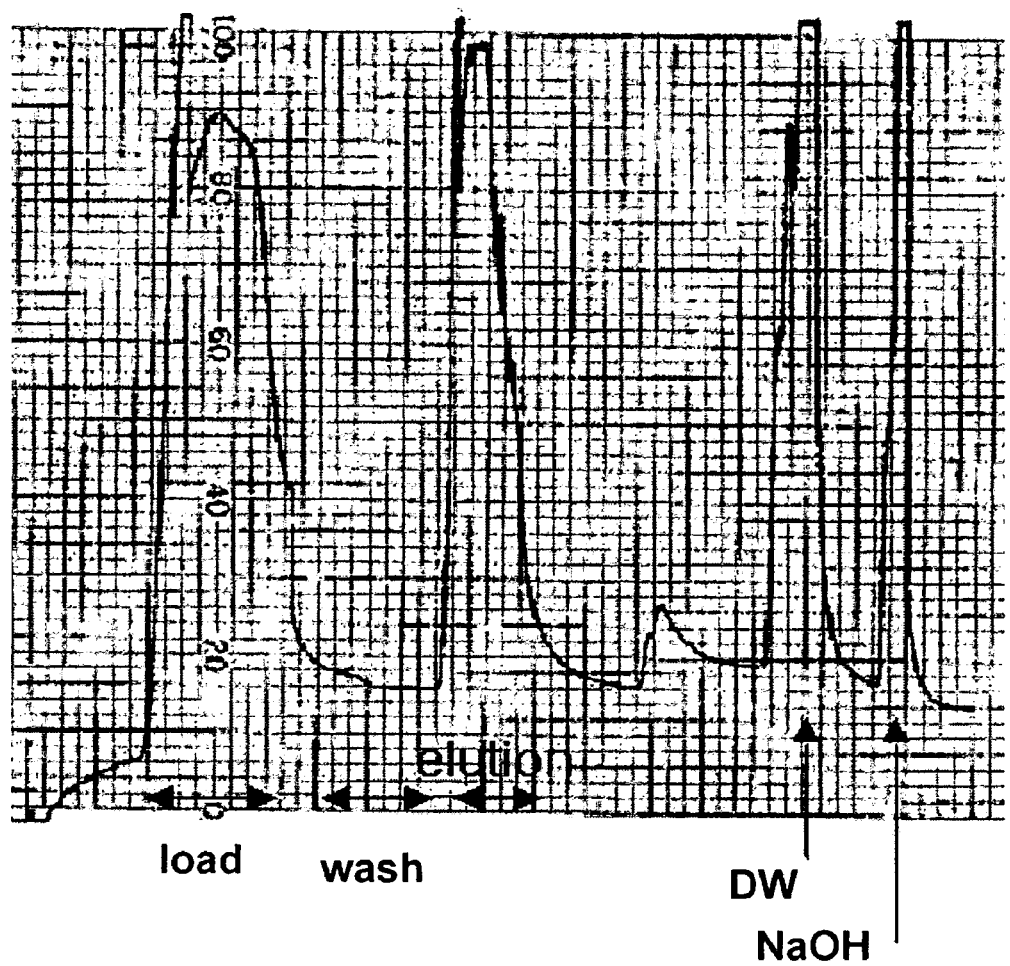
FIG. 13 is a chromatogram showing the specific purification of LK8 protein by hydrophobic interaction chromatography, in the middle of whole secretion and purification processes of LK8 protein:
Washing: 0.1-1 M of sodium phosphate solution;
Elution: 0.1-3 M of ammonium sulfate, 0.1-1 M of sodium phosphate, NaCl solution; and
Cleaning: NaCl solution.
Figure 14:
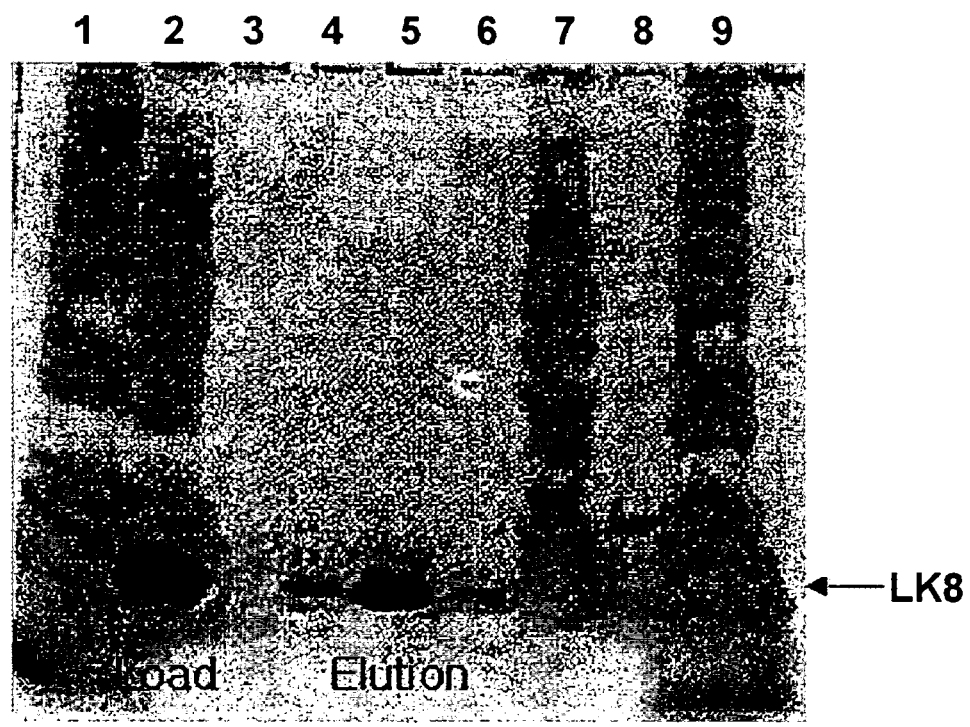
FIG. 14 is a photograph of PAGE showing the LK8 protein contents in each fraction of SP-phenylsepharose 6FF (fast flow) hydrophobic interaction chromatography:
Lane 1: Marker;
Lane 2: Sample eluted from SP-sepharose cation exchange resin;
Lane 3: Sample not attached resin;
Lane 4: Eluted fraction #1;
Lane 5: Eluted fraction #2;
Lane 6: Eluted fraction #3;
Lane 7: Sample eluted with sodium phosphate;
Lane 8: Sample eluted with distilled water; and
Lane 9: Ladder marker.

As confirmed from chromatogram (FIG. 13) and SDS-polyacryl amide gel electrophoresis (FIG. 14), most of impurities were eliminated by washing with 0.1-1 M sodium phosphate solution (pH 5-9) containing 0-2 M NaCl, and only LK8 protein was eluted from fraction by using ammonium sulfate and NaCl solution.

TABLE 2

|  | LK8(☐) | Recovery rate(%) |
|---|---|---|
| Loading | 204.3 | 100 |
| SP-sepharose FF | 160.6 | 80.1 |
| SP-phenylsepharose 6FF | 134.9 | 66 |

As explained hereinbefore, the recovery rate of purification of LK8 protein from the culture solution prepared in Example 7 by cation exchange chromatography was 80.1% and the recovery rate by hydrophobic interaction chromatography was 66% (Table 2).

INDUSTRIAL APPLICABILITY

As explained hereinbefore, a transformed strain was prepared by inserting chromosome integration cassette for LK8 gene expression into a *Saccharomyces cerevisiae* strain. LK8 gene could be expressed and secreted efficiently in a large-scale fermentor by providing the optimum conditions for batch-culture and fed-batch-culture of the above strain. By using the effective purification processes of the present invention, the mass production of LK8 protein can be achieved. Therefore, the transformed strain and production processes of LK8 protein of the present invention are expected to contribute greatly to the commercialization of LK8 protein as a novel angiogenesis inhibitor.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

Sequence Listing

SEQ ID No: 1 is a cDNA sequence coding the LK8 protein.

SEQ ID No: 2 is a DNA sequence coding the α-factor secretion signal of *S. cerevisiae*.

The invention claimed is:

1. A transformed *Saccharomyces cerevisiae* strain which is *Saccharomyces cerevisiae* BJ3501/MδLK8 #36 deposited under Accession No: KCTC 10582BP.

* * * * *